United States Patent [19]

Burns et al.

[11] 4,113,383
[45] Sep. 12, 1978

[54] METHOD AND APPARATUS FOR SOLUTE TRANSFER

[75] Inventors: Donald Arthur Burns, Putnam Valley; Henry Fontanilles, Fishkill, both of N.Y.

[73] Assignee: Technicon Instruments Corporation, Tarrytown, N.Y.

[21] Appl. No.: 749,558

[22] Filed: Dec. 10, 1976

[51] Int. Cl.² .................. G01N 1/00; G01N 21/26
[52] U.S. Cl. ........................... 356/36; 356/181; 422/65
[58] Field of Search ............... 356/36, 181; 23/253 R (U.S. only)

[56] References Cited

U.S. PATENT DOCUMENTS 3,566,677  3/1971  Cole et al. ............... 73/61.3

Primary Examiner—Vincent P. McGraw
Attorney, Agent, or Firm—S. P. Tedesco

[57] ABSTRACT

A liquid substance is transferred from a first carrier stream to a second carrier stream. The transfer includes the use of a movable conveyor and the flow of a deposited volume of the first stream along a portion of the conveyor as a sheath stream.

14 Claims, 3 Drawing Figures

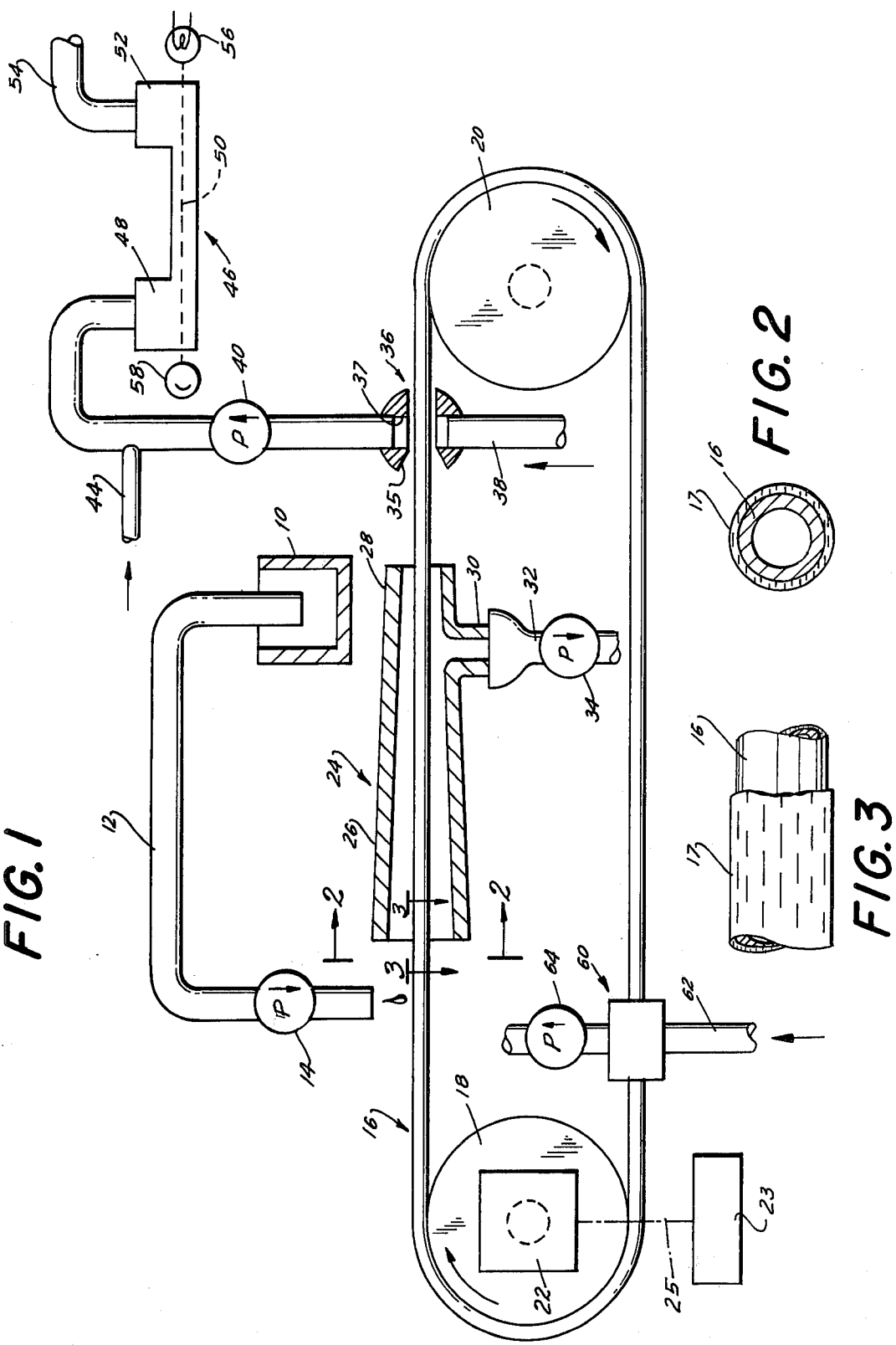

METHOD AND APPARATUS FOR SOLUTE TRANSFER

This invention relates generally to quantative analysis of a sample liquid, and relates more particularly to such an analysis of a series of liquid samples flowing seriatum, for example. However, it may be applied to a batch-type analysis or monitoring constituents in a stream. It further includes the analysis of a solute transferred from a first stream of liquid to a second stream of liquid, to meet in the latter the particular constituent and/or diluent requirements of a particular, known methodology of analysis of the sample. Still further, it involves in such transfer, evaporation to dryness of the solvent of the solute of interest from a first carrier liquid, usually in the form of an organic solvent. There follows prior to analysis, the eluting of the residue in the second stream comprising, among other constituents, a second eluting liquid carrier, usually an organic solvent, which may be the same as or different from the first carrier liquid, and if the same, in which the concentration of the solute is different from that which existed in the first stream.

In the drawings:

FIG. 1 is a somewhat diagrammatic view of apparatus embodying the invention;

FIG. 2 is an enlarged view taken on line 2—2 of FIG. 1; and

FIG. 3 is an elevational view taken on line 3—3 of FIG. 1 and broken away.

As shown in FIG. 1, by way of example, there is indicated a sample cup 10, one of a series of non-illustrated sampler supplying liquid samples one after another by aspiration into one end of a tube 12 in which tube there is interposed a continuously operating pump 14. The sampler may be of the type illustrated in U.S. Pat. No. 3,876,374. For example, the sample may be a vitamin in an organic eluting liquid or carrier of hexane utilized to extract the vitamin from another substance. As a series of eluate samples from successive samples are presented from successive cups to the aforementioned tube end, the first liquid stream flows along the tube 12. Between successive immersions in samples, said tube end aspirates air which provides gas segments in the stream in the tube 12 which occlude the latter and isolate the samples from each other.

The other end of tube 12 is fixedly supported by conventional means to discharge its contents directly upon a conveyor 16. The conveyor 16 according to one feature of the apparatus and technique, picks up the entire volume of the eluate, and to this end the carrier may be formed of a length of flexible circular tubing or rod stock such as Teflon for example, exhibiting a hydrophobic characteristic such that the discharge, through surface tension, completely encircles in continuous fashion such tubing exterior along a portion of the length thereof. Such encirclement is shown at 17 in FIG. 2. This tubing 16 may be continuous in the form of an endless loop trained over fixed pulleys 18, 20. The pulley 18 is driven by variable speed motor 22 through a conventional coupling, while the pulley 20 is an idler.

In one zone of the conveyor 16, the conveyor runs with considerable clearance through an evaporator tube, indicated generally at 24, generally of T form. The conveyor runs through the axially aligned lateral arms 26, 28 of the T which arms are open at their distal ends and serve to pass gas therethrough, such as air from the ambient atmosphere for example, as described hereinafter in more detail. The remaining arm 30 of the T may be connected to a vacuum source, and for this purpose, the outlet of arm 30 is coupled to the inlet end of tube 32 in which tube there is interposed a continuously operating pump 34. The tube 32 discharges in a non-illustrated manner to waste.

As shown in FIG. 1, the evaporator tube 24 has the arms 26, 28 merging into one another and may be of a funnel-shaped internal cross section converging in a direction away from the deposit of the first stream on the conveyor 16. Further, the arm 30 is located closer to the distal end of arm 28 than to the distal end of arm 26 so that air is drawn into the first-mentioned end at a higher velocity than that which is drawn into the distal end of arm 26. This provides assurance that the solvent in the first stream is completely evaporated to leave a residue from the solute on the conveyor 16, prior to the exit of the conveyor from the arm 28. In the form being described by way of example, it has been found unnecessary to heat the deposited first stream to evaporate the solvent to dryness on the conveyor. The solvent usually has a relatively low vaporization point. The evaporator tube 24, which may be structured of glass, is supported in fixed relation in a conventional way, not shown, and a transfer fitting 36 having cruciform passageways 35, 37 of the illustrated configuration is shown, which is fixed, through which the conveyor passes. The fitting 36 is located near the distal end of arm 28. The fitting 36, which is interposed in the tube 38, has an inlet in the passageway 37 coupled to an outlet of the tube 38 which tube 38 has an inlet end coupled in a non-illustrated manner to a source of liquid including, in this instance, the second organic solvent, e.g., methyl alcohol, of the second stream, which is different from the first organic solvent previously described. The solution, including the eluting liquid, from this source is caused to flow as a second stream in tube 38 by a variable speed pump 40 interposed in the tube 38. This second stream within the fitting 36 is caused by the latter to encircle the conveyor 16 with the aforementioned residue thereon and sweep such dissolving residue out of the fitting into the portion of tube 38 coupled to the discharge end of the passageway 37. Ambient air is sucked into passageways 35, 37 to segment the second stream flowing out of the fitting 36. Such gas forms occluding segments of the stream in the tube 38 which segments also isolate successive samples. Further, such segments also segment the second solvent stream which may flow continuously, including during intervals between samples. The fitting 36 has a funnel-shaped entrance aperture in the passageway 35 for the conveyor 16 with the residue thereon, for passage of the conveyor through the fitting as shown in FIG. 1. The exit portion of the passageway 35 for the conveyor more closely surrounds the conveyor, and this portion of the fitting 30 may serve as a guide for the conveyor 16 as it exits from the fitting 36.

A reagent may be added to the tube 38 through a tube 44 coupled to the tube 38 at its outlet end and having an inlet end immersed in a non-illustrated manner in such reagent.

In the illustrated form, the reagent reacts with the solute in the second stream flowing in tube 38 to provide a product the optical density of which is determined in the flow cell, indicated generally at 46, and having an inlet leg 48 coupled to the outlet of the tube 38. In conventional manner, the discharge from the tube 38 through the inlet leg 48 and a sight path 50 of the flow cell, and thence out the leg 52 of the cell is into the inlet end of tube 54 which has its discharge end directed to waste. A light source, in the form of a lamp 56 directs a ray of light along the sight path 50, which impinges upon a photodetector 58. The processed signal from the detector may be displayed in a conventional manner, not shown.

A fitting 60 identical to the above-described fitting 36, is interposed in another zone of the run of the conveyor 16, as shown in FIG. 1, for the purpose of washing the conveyor to eliminate any trace of residue thereon prior to the travel of the conveyor to the above-described deposit station. The fitting 60 is interposed in a tube 62, similar to the tube 38, which tube has a nonillustrated end immersed in a source of wash solution such the solvent of the above-described first stream, and a pump 64 is also interposed in the tube 62 for flowing the wash solution to the fitting 60 and around the conveyor 16 to clean it, prior to discharge to waste.

There are various modes of operation of the above-described apparatus. For example, the conveyor 16 may be stationary or nearly so as the first stream, including a sample, is deposited thereon, while the pump 34 is in operation to suck such deposit onto the conveyor and along a portion of the length of the conveyor as indicated in FIGS. 2 and 3. Evaporation of the carrier liquid commences on deposit of the first stream onto the conveyor 16 as a sheath stream flowing toward the fitting 36. If the conveyor 16 is stationary, i.e., the motor 22 is deenergized during such deposit, there is a build-up of residue on the conveyor. Then, when the conveyor is moved, the residue is carried by the conveyor to the fitting 36 where it is dissolved in the second stream flowing in tube 38. The motor 22 is controlled by programmer 23 having an output to the motor along lead 25. Alternatively, the motor may be operated continuously to drive the conveyor at relatively high speed, and the previously-described accumulation of the residue on a portion of the conveyor 16 is avoided and such avoidance eliminates a high concentration of the solute passing to the second stream through the fitting 36 when the speed of the pump 40 is continuous and at a normal speed. This results in a lesser concentration of the particular sample in the second stream than previously described. However, the speed of the pump 40 may be reduced or increased thereby affecting and changing the concentration of the sample in the second stream, i.e. increased or reduced, respectively.

Hereinbefore, the apparatus and the technique for transferring the solute from one stream to another has been described with reference to use of organic solvents. It is submitted that with the elongation of the conveyor 16 and the evaporator tube 24, such transfer including samples other than solutes may be effected utilizing aqueous solutions rather than organic solvents, to dry, for example, the carrier liquid of the first stream on the conveyor 16 prior to the elution of the residue in the second stream.

While several forms of the apparatus and method have been described, it will be apparent, especially to those versed in the art, that the solute transfer technique is susceptible of taking other forms and is susceptible to various changes in details without departing from the principles of the invention.

What is claimed is:

1. Apparatus transferring a substance from a first to a second liquid stream, comprising: means flowing said first stream from a source to a first station and depositing it upon a conveyor movable from said first station to a second station, means to move said conveyor, means flowing said second stream to said second station to pick up said substance, means to flow said deposited first stream along at least a portion of the conveyor from said first station toward said second station, and means to actuate said conveyor-moving means.

2. Apparatus as defined in claim 1, wherein: said substance is a solute, said means flowing said deposited first stream comprising an evaporator tube through which said conveyor moves.

3. Apparatus as defined in claim 1, wherein: said substance is a liquid sample, and further including analysis means downstream from said second station analyzing said sample.

4. Apparatus as defined in claim 1, wherein: said conveyor is structured of an elongated element having a uniform relatively smooth longitudinal exterior on which said deposit is made.

5. Apparatus as defined in claim 2, wherein: said evaporator tube is funnel-shaped and funnels a drying gas therethrough to a vacuum outlet of said tube.

6. Apparatus as defined in claim 2, wherein: said evaporator tube is of T form, and a solvent of said solute is evaporated to dryness prior to arrival at said second station.

7. Apparatus as defined in claim 4, wherein: said elongated element has a periphery which in cross section is circular.

8. A method of transferring a substance from a first to a second liquid stream, comprising: flowing said first stream from a source to a first station and depositing it upon a conveyor movable from said first station to a second station, flowing said second stream to said second station to pick up said substance, flowing said deposited first stream along at least a portion of the conveyor from said first station toward said second station, and moving the conveyor to said second station.

9. A method as defined in claim 8, wherein: said substance is a solute in a solvent, and evaporating said solvent to dryness while moving said conveyor to said second station.

10. A method as defined in claim 8, wherein: said substance is a liquid sample, and further including analyzing said sample downstream from said second station.

11. A method as defined in claim 8, wherein said flowing of said deposited first stream on said conveyor comprises drawing said stream along a portion of said conveyor as a sheath stream.

12. A method as defined in claim 8, wherein: the volumetric flow of said first and second streams is varied one to the other to change the concentration of said substance in said second stream.

13. A method as defined in claim 9, wherein: said evaporating step comprises funneling a drying gas along a portion of said conveyor.

14. A method as defined in claim 9, wherein: said solute is evaporated to dryness while said conveyor is moving to said second station.

* * * * *